United States Patent [19]
Farascioni

[11] Patent Number: 6,019,733
[45] Date of Patent: Feb. 1, 2000

[54] BIOPSY APPARATUS AND METHOD

[75] Inventor: David Farascioni, Bethel, Conn.

[73] Assignee: United States Surgical Corporation, Norwalk, Conn.

[21] Appl. No.: 09/157,042

[22] Filed: Sep. 18, 1998

Related U.S. Application Data

[60] Provisional application No. 60/059,546, Sep. 19, 1997.

[51] Int. Cl.$^7$ .................................................. A61B 10/00
[52] U.S. Cl. ........................... 600/564; 600/567; 606/167
[58] Field of Search .................................... 600/562, 564, 600/565, 566, 567, 568; 604/22; 606/167, 170, 181, 184, 185

[56] References Cited

U.S. PATENT DOCUMENTS

| Re. 33,258 | 7/1990 | Onik et al. ................................. | 604/22 |
| Re. 34,056 | 9/1992 | Lindgren et al. ........................ | 128/754 |
| 737,293 | 8/1903 | Summerfeldt ............................ | 606/159 |
| 1,585,934 | 5/1926 | Muir ......................................... | 600/567 |
| 1,663,761 | 3/1928 | Johnson .................................... | 606/159 |

(List continued on next page.)

FOREIGN PATENT DOCUMENTS

| 0 010 321 A1 | 4/1980 | European Pat. Off. . |
| 0 019 104 | 11/1980 | European Pat. Off. . |
| 0 207 726 A2 | 1/1987 | European Pat. Off. . |
| 0 238 461 A1 | 9/1987 | European Pat. Off. . |
| 0 378 692 | 7/1990 | European Pat. Off. . |

(List continued on next page.)

OTHER PUBLICATIONS

Automatic Soft Tissue Biopsy System, (ASAP™) Operational Guidelines, Microvasive Boston Scientific Corp., (2 pgs.).

When it Comes to Core Samples, I Demand Accuracy and Consistency for All My Patients, The Bard Biopty Biopsy System, Bard® Radiology, (4 pgs).

Nucleotome® System Automated Percutaneous Lumbar Disectomy, Surgical Dyamics®, (3 pgs.).

Introducing the Singular Technology for Multi–Core Microcalcification sampling, Biopsys Medical Inc., (2 pgs).

Mammotome Multi–Probe, Probe and Motorized Driver, Instructions for Use, Biopsys Medical Inc., (3 pgs.).

Stereotaxic Needle Core Biopsy of Breast Lesions Using a Regular Mammographic Table with an Adaptable Stereotaxic Device, Caines et al., pp. 317–321, Aug. 1993.

Stereotactic Breast Biopsy with a Biopsy Gun, Parker, MD et al., pp. 741–747, Sep. 1990.

Stereotactic Percutaneous Breast Core Biopsy Technical Adaptation and Inital Experience, Lovin, MD et al., pp. 135–143, 1990.

Selective Use of Image–Guided Large–Core Needle Biopsy of the Breast: Accuracy and Cost–Effectiveness, Doyle et al., pp. 281–284, Aug. 1995.

Breast Biopsy: A Comparative Study of Stereotaxially Guided Core and Excisional Techniques, Gisvold et al., pp. 815–820, Apr., 1994.

Sterotactic Core Needle Biopsy of Mammographic Breast Lesions as a Viable Alternative to Surgical Biopsy, Mikhail, MD et al., pp. 363–367, 1994.

Primary Examiner—Cary O'Connor
Assistant Examiner—Charles Marmor, II

[57] ABSTRACT

An apparatus and method for the biopsy of tissue specimens and, more particularly, a single insertion multiple sample percutaneous biopsy apparatus and method are provided. A tip at a distal end of a support tube is introduced into a tissue mass. The support tube has a lateral opening adjacent the tip. A knife tube is disposed within the support tube and is retracted allowing the lateral opening to communicate with the tissue mass. Suction through a suction tube draws tissue into the lateral opening where it is severed placing the tissue in a pusher. Pusher is attached to vacuum tube which is retracted proximally through the knife tube. A tissue sample is drawn through the knife tube to a location where it can be removed from the pusher.

11 Claims, 3 Drawing Sheets

6,019,733
Page 2

U.S. PATENT DOCUMENTS

| | | | |
|---|---|---|---|
| 1,867,624 | 7/1932 | Hoffman | 600/567 |
| 2,729,210 | 1/1956 | Spencer | 600/564 |
| 3,400,708 | 9/1968 | Scheidt | 128/2 |
| 3,477,423 | 11/1969 | Griffith | 128/2 |
| 3,561,429 | 2/1971 | Jewett et al. | 128/2 |
| 3,590,808 | 7/1971 | Muller | 128/2 B |
| 3,606,878 | 9/1971 | Kellogg, Jr. | 128/2 B |
| 3,732,858 | 5/1973 | Banko | 128/2 B |
| 3,734,099 | 5/1973 | Bender et al. | 128/305 |
| 3,844,272 | 10/1974 | Banko | 128/2 B |
| 3,929,123 | 12/1975 | Jamshidi | 128/2 B |
| 3,989,033 | 11/1976 | Halpern | 128/2 B |
| 3,995,619 | 12/1976 | Glatzer | 128/2 B |
| 4,099,518 | 7/1978 | Baylis et al. | 128/2 B |
| 4,200,106 | 4/1980 | Douvas et al. | 128/305 |
| 4,203,444 | 5/1980 | Bonnell et al. | 128/276 |
| 4,210,146 | 7/1980 | Banko | 128/305 |
| 4,340,066 | 7/1982 | Shah | 128/749 |
| 4,396,021 | 8/1983 | Baumgartner | 128/754 |
| 4,600,014 | 7/1986 | Beraha | 128/754 |
| 4,644,951 | 2/1987 | Bays | 128/305 |
| 4,651,753 | 3/1987 | Lifton | 128/751 |
| 4,660,267 | 4/1987 | Wheeler | 29/437 |
| 4,662,869 | 5/1987 | Wright | 604/22 |
| 4,674,502 | 6/1987 | Imonti | 128/305 |
| 4,681,123 | 7/1987 | Valtchev | 128/753 |
| 4,699,154 | 10/1987 | Lindgren | 128/754 |
| 4,702,260 | 10/1987 | Wang | 128/753 |
| 4,702,261 | 10/1987 | Cornell et al. | 128/754 |
| 4,708,147 | 11/1987 | Haaga | 128/753 |
| 4,711,250 | 12/1987 | Gilbaugh, Jr. et al. | 128/765 |
| 4,733,671 | 3/1988 | Mehl | 128/754 |
| 4,735,215 | 4/1988 | Goto et al. | 128/754 |
| 4,776,346 | 10/1988 | Beraha et al. | 128/754 |
| 4,781,202 | 11/1988 | Janese | 128/754 |
| 4,799,494 | 1/1989 | Wang | 128/753 |
| 4,838,280 | 6/1989 | Haaga | 128/751 |
| 4,844,088 | 7/1989 | Kambin | 128/753 |
| 4,874,375 | 10/1989 | Ellison | 604/164 |
| 4,881,551 | 11/1989 | Taylor | 128/754 |
| 4,907,598 | 3/1990 | Bauer | 128/753 |
| 4,907,599 | 3/1990 | Taylor | 128/754 |
| 4,917,100 | 4/1990 | Nottke | 128/749 |
| 4,924,878 | 5/1990 | Nottke | 128/751 |
| 4,936,835 | 6/1990 | Haaga | 604/265 |
| 4,940,061 | 7/1990 | Terwilliger et al. | 128/754 |
| 4,944,308 | 7/1990 | Akerfeldt | 128/751 |
| 4,953,558 | 9/1990 | Akerfeldt | 128/751 |
| 4,958,625 | 9/1990 | Bates et al. | 128/754 |
| 4,976,269 | 12/1990 | Mehl | 128/754 |
| 4,989,614 | 2/1991 | Dejter, Jr. et al. | 128/752 |
| 4,991,592 | 2/1991 | Christ | 128/754 |
| 5,031,634 | 7/1991 | Simon | 128/754 |
| 5,036,860 | 8/1991 | Leigh et al. | 128/754 |
| 5,047,008 | 9/1991 | de Juan, Jr. et al. | 604/22 |
| 5,048,538 | 9/1991 | Terwilliger | 128/754 |
| 5,080,655 | 1/1992 | Haaga | 604/265 |
| 5,106,364 | 4/1992 | Hayafuji et al. | 604/22 |
| 5,121,751 | 6/1992 | Panalletta | 128/754 |
| 5,127,419 | 7/1992 | Kaldany | 128/754 |
| 5,146,921 | 9/1992 | Terwilliger et al. | 128/754 |
| 5,183,052 | 2/1993 | Terwilliger et al. | 128/753 |
| 5,183,054 | 2/1993 | Burkholder et al. | 128/754 |
| 5,188,118 | 2/1993 | Terwilliger | 128/753 |
| 5,195,533 | 3/1993 | Chin et al. | 128/754 |
| 5,195,988 | 3/1993 | Haaga | 604/265 |
| 5,199,441 | 4/1993 | Hogle | 128/753 |
| 5,213,110 | 5/1993 | Kedem et al. | 128/754 |
| 5,220,926 | 6/1993 | Jones | 128/754 |
| 5,224,488 | 7/1993 | Neuffer | 128/751 |
| 5,226,909 | 7/1993 | Evans et al. | 606/159 |
| 5,226,910 | 7/1993 | Kajiyama et al. | 606/171 |
| 5,234,994 | 8/1993 | Shiraki et al. | 525/92 |
| 5,249,582 | 10/1993 | Taylor | 128/754 |
| 5,249,583 | 10/1993 | Mallaby | 128/754 |
| 5,254,105 | 10/1993 | Haaga | 604/265 |
| 5,273,051 | 12/1993 | Wilk | 128/751 |
| 5,282,476 | 2/1994 | Terwilliger | 128/753 |
| 5,284,156 | 2/1994 | Schramm et al. | 128/754 |
| 5,285,795 | 2/1994 | Ryan et al. | 128/750 |
| 5,290,303 | 3/1994 | Pingleton et al. | 606/170 |
| 5,301,684 | 4/1994 | Ogirala | 128/754 |
| 5,313,958 | 5/1994 | Bauer | 128/754 |
| 5,316,013 | 5/1994 | Striebel, II et al. | 128/754 |
| 5,320,110 | 6/1994 | Wang | 128/753 |
| 5,368,045 | 11/1994 | Clement et al. | 128/754 |
| 5,415,182 | 5/1995 | Chin et al. | 128/754 |
| 5,425,376 | 6/1995 | Banys et al. | 128/753 |
| 5,458,112 | 10/1995 | Weaver | 128/753 |
| 5,476,101 | 12/1995 | Schramm et al. | 128/754 |
| 5,477,862 | 12/1995 | Haaga | 128/754 |
| 5,492,130 | 2/1996 | Chiou | 128/753 |
| 5,505,210 | 4/1996 | Clement | 600/566 |
| 5,505,211 | 4/1996 | Ohto et al. | 128/754 |
| 5,511,556 | 4/1996 | DeSantis | 128/754 |
| 5,526,822 | 6/1996 | Burbank et al. | 128/754 |
| 5,535,755 | 7/1996 | Heske | 128/754 |
| 5,546,957 | 8/1996 | Heske | 128/754 |
| 5,560,373 | 10/1996 | De Santis | 128/753 |
| 5,564,436 | 10/1996 | Hakky et al. | 600/567 |
| 5,649,547 | 7/1997 | Richart et al. | 128/754 |
| 5,655,542 | 8/1997 | Weilandt | 128/754 |
| 5,752,923 | 5/1998 | Terwilliger | 600/562 |
| 5,769,086 | 6/1998 | Ritchart et al. | 128/753 |
| 5,775,333 | 7/1998 | Burbank et al. | 128/754 |
| 5,779,647 | 7/1998 | Chau et al. | 600/564 |
| 5,782,764 | 7/1998 | Werne | 600/567 |
| 5,782,849 | 7/1998 | Miller | 606/159 |
| 5,794,626 | 8/1998 | Kieturakis | 600/567 |
| 5,817,033 | 10/1998 | DeSantis et al. | 600/562 |
| 5,823,970 | 10/1998 | Terwilliger | 600/567 |
| 5,842,999 | 12/1998 | Pruitt et al. | 600/567 |
| 5,873,886 | 2/1999 | Larsen et al. | 606/180 |
| 5,876,369 | 3/1999 | Houser | 606/167 |
| 5,928,218 | 7/1999 | Gelbfish | 604/22 |
| 5,944,673 | 8/1999 | Gregoire et al. | 600/564 |

FOREIGN PATENT DOCUMENTS

| | | |
|---|---|---|
| 0 442 851 A1 | 8/1991 | European Pat. Off. . |
| 0 536 888 A1 | 4/1993 | European Pat. Off. . |
| 0 561 732 A1 | 9/1993 | European Pat. Off. . |
| 1 161 400 | 8/1958 | France . |
| 1 267 960 | 6/1960 | France . |
| 2 332 743 | 6/1977 | France . |
| 2 654 609 | 5/1991 | France . |
| 935 625 | 11/1955 | Germany . |
| 1 817 555 | 1/1971 | Germany . |
| 27 19 959 A1 | 11/1978 | Germany . |
| 159 394 | 3/1983 | Germany . |
| 42 16 694 A1 | 12/1992 | Germany . |
| 400319 | 2/1974 | U.S.S.R. . |
| 520 976 | 7/1976 | U.S.S.R. . |
| 648 219 | 2/1979 | U.S.S.R. . |
| 707 576 | 1/1980 | U.S.S.R. . |
| 0728 852 | 5/1980 | U.S.S.R. . |
| 1178 422 | 9/1985 | U.S.S.R. . |
| 1192 795 | 11/1985 | U.S.S.R. . |
| 1 255 330 | 12/1971 | United Kingdom . |
| 1 393 068 | 5/1975 | United Kingdom . |
| 2 237 992 | 5/1991 | United Kingdom . |
| WO 91/01112 | 2/1991 | WIPO . |
| WO 92/00040 | 1/1992 | WIPO . |

| | | | | | | |
|---|---|---|---|---|---|---|
| WO 92/19159 | 11/1992 | WIPO . | | WO 93/20753 | 10/1993 | WIPO . |
| WO 93/12707 | 7/1993 | WIPO . | | WO 94/08512 | 4/1994 | WIPO . |
| WO 93/14707 | 8/1993 | WIPO . | | WO 94/26172 | 11/1994 | WIPO . |
| WO 83/03343 | 10/1993 | WIPO . | | WO 88/07839 | 10/1998 | WIPO . |

BIOPSY APPARATUS AND METHOD

CROSS REFERENCE TO RELATED APPLICATION

This application claims priority to U.S. Provisional Application Ser. No. 60/059,546 filed Sep. 19, 1997 by Farascioni, the entire contents of which are hereby incorporated by reference.

BACKGROUND

1. Technical Field

This disclosure relates to an apparatus and method for the biopsy of tissue specimens and, more particularly, to a single insertion, multiple sample percutaneous biopsy apparatus and method.

2. Background of Related Art

It is often necessary to sample tissue in order to diagnose and treat patients suspected of having cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via frozen section or paraffin section. In more recent developments percutaneous techniques have been used to remove the entire mass during the initial procedure.

The type of biopsy utilized depends in large part on the circumstances present with respect to the patient and no single procedure is ideal for all cases. Core biopsy, however, is extremely useful in a number of conditions and is being used more frequently.

Intact tissue from the organ or lesion is preferred by medical personnel in order to arrive at a definitive diagnosis regarding the patient's condition. In most cases only part of the organ or lesion need be sampled. The portions of tissue extracted must be indicative of the organ or lesion as a whole. In the past, to obtain adequate tissue from organs or lesions within the body, surgery was performed so as to reliably locate, identify and remove the tissue. With present technology, medical imaging equipment such as stereotactic x-ray, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

Mammography can identify non-palpable (not perceptible by touch) breast abnormalities earlier than they can be diagnosed by physical examination. Most non-palpable breast abnormalities are benign but some are malignant. When breast cancer is diagnosed before it becomes palpable, breast cancer mortality can be reduced. It is still difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope.

The introduction of stereotactic guided percutaneous breast biopsies offered alternatives to open surgical breast biopsy. With time, these guidance systems have become more accurate and easier to use. Biopsy guns were introduced for use in conjunction with these guidance systems. Accurate placement of the biopsy guns was important to obtain useful biopsy information because only one small core could be obtained per insertion at any one location. To sample the lesion thoroughly, many separate insertions of the instrument had to be made.

Biopsy procedures may benefit from larger tissue samples being taken, for example, tissue samples as large as 10 mm across. Many of the prior art devices required multiple punctures into the breast or organ in order to obtain the necessary samples. This practice is both tedious and time consuming.

One further solution to obtain a larger tissue sample is to utilize a device capable of taking multiple tissue samples with a single insertion of an instrument. An example of such a device is found in U.S. Pat. No. 5,195,533 to Chin et al. which describes a technique for extracting multiple samples with a single insertion of the biopsy device. Generally, such biopsy instruments extract a sample of tissue from a tissue mass by either drawing a tissue sample into a hollow needle via an external vacuum source or by severing and containing a tissue sample within a notch formed on a stylet. Typical of such devices utilizing an external vacuum source are U.S. Pat. No. 5,246,011 issued to Cailouette and U.S. Pat. No. 5,183,052 issued to Terwiliger. Such devices generally contemplate advancing a hollow needle into a tissue mass and applying a vacuum force to draw a sample into the needle and hold the same therein while the tissue is extracted.

When extracting multiple samples with a single insertion of the biopsy device using suction to either draw in tissue or remove the tissue from the body, it is important that the vacuum path remain unclogged. If the vacuum path clogs, the sample removal will become difficult or impossible. This may necessitate multiple insertions of the device or reduce the sample mass per extraction.

Therefore, a continuing need exists for percutaneous biopsy apparatus and methods which can reliably extract adequate biopsy sample(s) with a single insertion of the biopsy instrument.

SUMMARY

The present disclosure describes an apparatus and method for the biopsy of tissue specimens and, more particularly, to a single insertion multiple sample percutaneous biopsy apparatus and method. A tip at a distal end of a support tube is introduced into a tissue mass. The support tube has a lateral opening adjacent the tip. A knife tube is disposed within the support tube and is retracted allowing the lateral opening to communicate with the tissue mass. Suction through a suction tube draws tissue into the lateral opening where it is severed placing the tissue in a pusher. Pusher is attached to vacuum tube which is retracted proximally through the knife tube. A tissue sample is drawn through the knife tube to a location where it can be removed from the pusher.

The surgical biopsy apparatus disclosed comprises a housing, a first elongated tubular member slidably and rotatably mounted in the housing and defining a fluid passageway therewithin. The first elongated tubular member includes a tissue receiver fixedly attached to the distal end of the first elongated tubular member. The tissue receiver defines a laterally disposed tissue receiving opening which includes a tissue support surface defining a plurality of transverse openings in fluid communication with the fluid passageway.

The apparatus further includes a second elongated tubular member slidably and rotatably disposed coaxially about the first elongated tubular member. The second elongated tubular member has a cutting surface formed at its distal end.

A third elongated tubular member is also included and is rotatably mounted to the housing and rotatably coaxially disposed about the first and second elongated tubular members. The third elongated tubular member includes a distal tip portion adapted to penetrate tissue and a lateral opening formed adjacent its distal end. The first elongated tubular member is movable from a retracted position to an extended position wherein the lateral opening of the third elongated tubular member is substantially aligned and in fluid communication with the tissue receiving portion of the first elongated tubular member. Preferably, the tissue receiver has a detent protruding therefrom and the distal tip portion defines a slot for receiving the detent.

In a preferred embodiment, the third elongated tubular member includes a control member fixedly mounted to its proximal end. The control member and the proximal end of the third elongated tubular member are preferably rotatably mounted to a distal end of the housing.

In another preferred embodiment, the housing defines a first bore configured and dimensioned to receive the second elongated tubular member. In another preferred embodiment, the housing defines a bore configured and dimensioned to receive a gear shaft wherein a gear is mounted to the gear shaft and the second elongated tubular member is positioned therewithin and cooperatively engages the gear. Preferably, the housing includes an intermediate portion defining a first and a second surface for movement of the gear therebetween, the movement of the gear between the first and second surfaces allows translation and rotation of the gear shaft and the second elongated member.

In yet another embodiment, the housing defines a second bore configured and dimensioned for receiving the tissue receiver. It is also envisioned that the housing may define a third bore configured and dimensioned for receiving the first elongated tubular member.

Desirably, a vacuum port is removably mounted to the proximal end of the first elongated tubular member. Most desirably, the housing further defines a tissue receptacle portion for discharging a tissue sample.

A method of performing a surgical biopsy is disclosed comprising the steps of: inserting a biopsy apparatus into the tissue of a patient, the biopsy apparatus including a housing, a first elongated tubular member defining a fluid passageway therewithin and having a tissue receiver, a second elongated tubular member having a cutting edge formed at an open distal end thereof, and a third elongated tubular member having a distal tip portion and a lateral opening; applying suction to a series of openings formed along an inner surface of the tissue receiver to pull tissue into the tissue receiver; severing tissue disposed within the tissue receiver by advancing the second elongated tubular member over the first elongated tubular member such that a cutting surface formed on the distal end of the second elongated tubular member rotates as it passes over the tissue receiver; and removing the severed tissue sample from a tissue sampling site by retracting the first elongated tubular member within the second and third elongated tubular members until the tissue receiver is substantially aligned with a lateral opening formed in the housing wherein a tissue sample is urged out of the tissue receiver.

BRIEF DESCRIPTION OF THE DRAWINGS

Various embodiments are described herein with reference to the drawings, wherein.

DETAILED DESCRIPTION OF PREFERRED EMBODIMENTS

Figure 1:
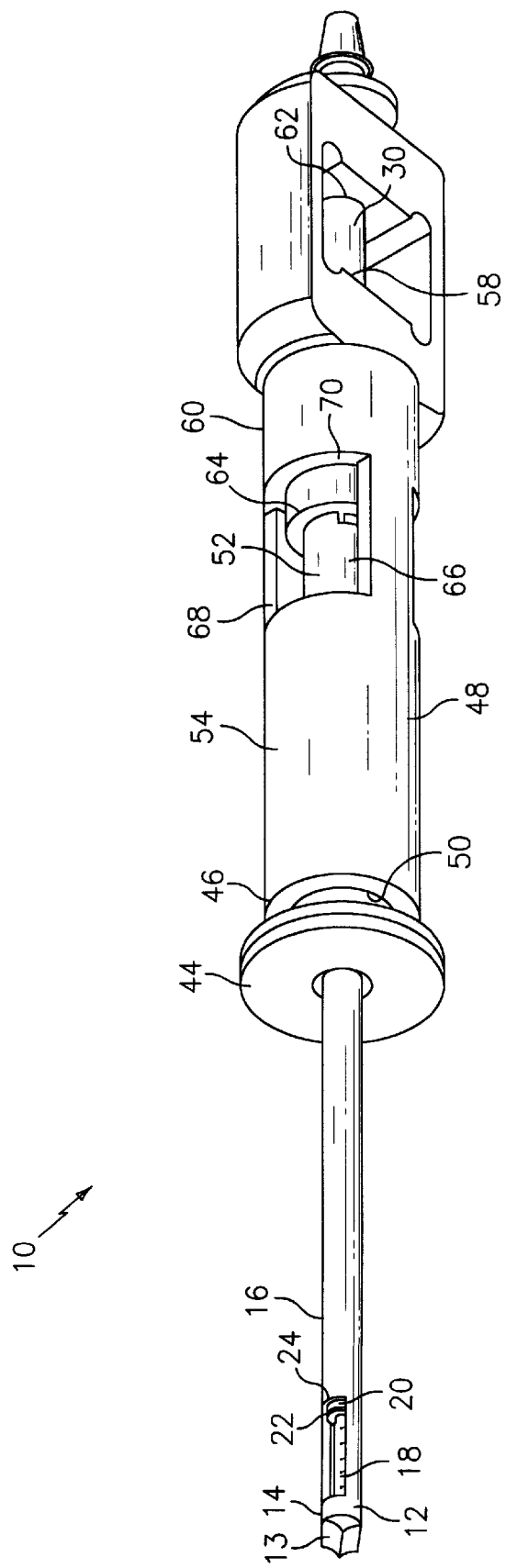
FIG. 1 is a perspective view of a biopsy apparatus.

Referring now in specific detail to the drawings in which like reference numerals identify similar or identical elements throughout the several views, and initially to FIG. 1, a biopsy apparatus constructed in accordance with the present disclosure is shown generally at 10. Biopsy apparatus 10 includes a tip portion 12 rigidly mounted to a distal end 14 of a support tube 16. Support tube 16 defines a lateral opening 18 therein proximal to tip portion 12. A knife tube 20 is slidably and rotatably disposed within the support tube 16. Knife tube 20 has a knife edge 22 disposed about a distal end 24.

Figure 2:
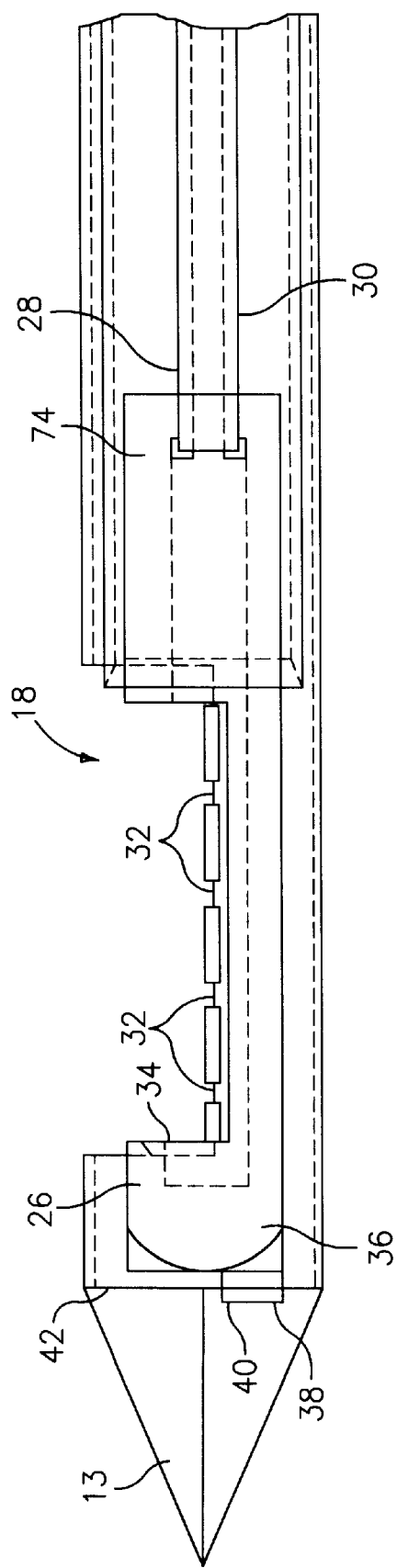
FIG. 2 is an enlarged side view of a tip portion of the biopsy apparatus of FIG. 1.

Referring to FIG. 2, a pusher 26 is attached to a distal end 28 of a suction tube 30. Suction tube 30 and pusher 26 are configured and dimensioned to fit within knife tube 20. Pusher 26 is positioned in communication with lateral opening 18. Pusher 26 defines a plurality of transverse holes 32 therethrough in communication with suction tube 30. Pusher 26 forms a tissue basket 34 thereon for receiving tissue therein during operation. A distal end 36 of pusher 26 has a tab 38 protruding therefrom. Tab 38 is received within a slot 40 formed in a proximal end portion 42 of a tip 13 in order to provide support for pusher 26 during operation.

Referring again to FIG. 1, support tube 16 mounts a wheel 44 at a proximal end thereof. Wheel 44 is rigidly attached and provides a means in which to adjust and rotate support tube 16. Wheel 44 and support tube 16 rotatably attach to a distal end 46 of a body 48. Body 48 defines a first bore 50 for receiving a gear shaft 52 therein at a distal end portion 54. Knife tube 20 is configured and dimensioned to fit within gear shaft 52 and is rigidly mounted therein. Body 48 defines a second bore 58 for passing suction tube 30 and pusher 26 therethrough at an intermediate portion 60. Body 48 further defines a third bore 62 dimensioned and configured to allow only suction tube 30 to pass therethrough.

A gear 64 is mounted on gear shaft 52 and disposed within intermediate portion 60 of body 48. Intermediate portion 60 has a slot 66 therein dimensioned and configured to allow the translation and rotation of gear 64 and gear shaft 52. Gear 64 translates between a first wall 68 and a second wall 70 spaced apart such that gear translation extremes are defined by the spacing between first wall 68 and second wall 70. Gear 64 is used to control the translation and rotation of gear shaft 52 and knife tube 20.

Figure 3:
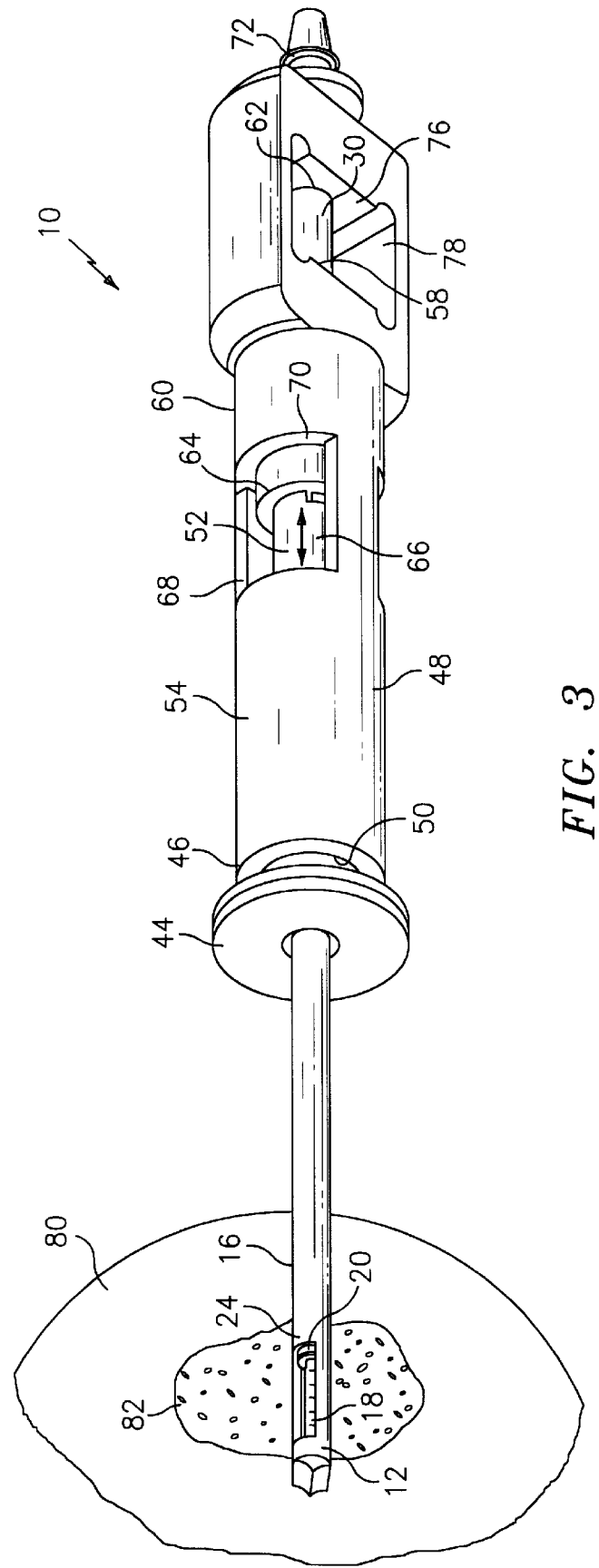
FIG. 3 is a perspective view of the biopsy apparatus of FIG. 1 showing the tip portion inserted in breast tissue.

Referring to FIG. 3, during a biopsy procedure, breast tissue 80 is clamped to prevent movement thereof during the procedure. An incision in breast tissue 80 is provided to aid in the insertion of biopsy apparatus 10. Biopsy apparatus 10 is aligned with a target tissue mass 82 inside breast tissue 80. Knife tube 20 is fully advanced distally to close lateral opening 18. Tip portion 12 is inserted into breast tissue 80 and moved distally such that target tissue mass 82 is adjacent to lateral opening 18. Knife tube 20 is retracted to expose lateral opening 18 to target tissue mass 82. Suction is applied through a suction knob 72, suction tube 30, pusher 26 and lateral opening 18. Tissue is drawn into lateral opening 18 and engages pusher 26.

Knife tube 20 is advanced distally while simultaneously being rotated. The motion of knife tube 20 severs target tissue mass 82 to create a tissue sample. When knife tube 20 is fully advanced distally, the tissue sample is severed and is disposed within pusher 26. Suction tube 30 is retracted proximally through first bore 50 and second bore 58 of body 48. A proximal end 74 of pusher 26 engages a wall 76 which prevents further proximal translation. Pusher 26 is held above a tissue receptacle portion 78 of body 48. Suction is removed and tissue sample can now be removed from pusher 26.

Pusher 26 may now be readvanced into breast 80. An additional tissue sample or samples may be obtained from the same location as the previous sample, for example, to completely remove a tissue mass, or support tube 16 may be rotated to allow lateral opening 18 to face another region in from which tissue may be sampled. By reintroducing pusher 26 additional samples can be obtained through a single insertion into the breast tissue.

It will be understood that various modifications may be made to the embodiments disclosed herein. Therefore, the above description should not be construed as limiting, but merely as exemplifications of preferred embodiments.

What is claimed is:

1. A surgical biopsy apparatus, comprising:
    a housing;
    a first elongated tubular member slidably and rotatably mounted in the housing, the first elongated tubular member having a proximal end and a distal end and defining a fluid passageway therewithin, the first elongated tubular member including:
    a tissue receiver fixedly attached to the distal end of the first elongated tubular member, the tissue receiver defining a laterally disposed tissue receiving opening which includes a tissue support surface defining a plurality of transverse openings in fluid communication with the fluid passageway;
    a second elongated tubular member slidably and rotatably disposed coaxially about the first elongated tubular member, second elongated tubular member having a cutting surface formed at the distal end thereof;
    a third elongated tubular member having a proximal and a distal end, the third elongated member rotatably mounted to the housing and rotatably coaxially disposed about the first and second elongated tubular members, the third elongated tubular member including:
        a distal tip portion adapted to penetrate tissue; and
        a lateral opening formed adjacent the distal end of the third elongated tubular member,
        the first elongated tubular member being movable from a retracted position to an extended position wherein the lateral opening of the third elongated tubular member is substantially aligned and in fluid communication with the tissue receiving portion of the first elongated tubular member.

2. The surgical apparatus according to claim 1, wherein the tissue receiver has a detent protruding therefrom and the distal tip portion defines a slot for receiving the detent.

3. The surgical apparatus according to claim 1, wherein the third elongated tubular member further includes a control member fixedly mounted to the proximal end thereof, the control member and the proximal end of the third elongated tubular member being rotatably mounted to a distal end of the housing.

4. The surgical apparatus according to claim 1, wherein the housing defines a first bore configured and dimensioned to receive the second elongated tubular member.

5. The surgical apparatus according to claim 1, wherein the housing defines a first bore configured and dimensioned to receive a gear shaft wherein a gear is mounted to the gear shaft and the second elongated tubular member is positioned therewithin and cooperatively engages the gear.

6. The surgical apparatus according to claim 5, wherein the housing further includes an intermediate portion defining a first and a second surface for movement of the gear therebetween, the movement of the gear between the first and second surfaces allowing translation and rotation of the gear shaft and the second elongated member.

7. The surgical apparatus according to claim 1, wherein the housing defines a second bore configured and dimensioned for receiving the tissue receiver.

8. The surgical apparatus according to claim 1, wherein the housing defines a third bore configured and dimensioned for receiving the first elongated tubular member.

9. The surgical apparatus according to claim 1, further comprising a vacuum port removably mounted to the proximal end of the first elongated tubular member.

10. The surgical apparatus according to claim 1, wherein the housing further defines a tissue receptacle portion for discharging a tissue sample.

11. A method of performing a surgical biopsy comprising the steps of:
    inserting a biopsy apparatus into the tissue of a patient, the biopsy apparatus including:
        a housing,
        a first elongated tubular member defining a fluid passageway therewithin and having a tissue receiver,
        a second elongated tubular member having a cutting surface formed at an open distal end thereof, and
        a third elongated tubular member having a distal tip portion and a lateral opening;
    applying suction to a series of openings formed along an inner surface of the tissue receiver to pull tissue into the tissue receiver;
    severing tissue disposed within the tissue receiver by advancing the second elongated tubular member over the first elongated tubular member such that a cutting surface formed on the distal end of the second elongated tubular member rotates as it passes over the tissue receiver; and
    removing the severed tissue sample from a tissue sampling site by retracting the first elongated tubular member within the second and third elongated tubular members until the tissue receiver is substantially aligned with a lateral opening formed in the housing wherein a tissue sample is urged out of the tissue receiver.

* * * * *